United States Patent
Bugni et al.

(10) Patent No.: US 12,240,859 B2
(45) Date of Patent: Mar. 4, 2025

(54) TURBINMICIN COMPOUNDS, COMPOSITIONS AND USES THEREOF

(71) Applicant: Wisconsin Alumni Research Foundation, Madison, WI (US)

(72) Inventors: Timothy Bugni, Madison, WI (US); Fan Zhang, Madison, WI (US); Douglas R. Braun, Mount Horeb, WI (US); David Andes, Verona, WI (US); Miao Zhao, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 851 days.

(21) Appl. No.: 17/420,117

(22) PCT Filed: Dec. 27, 2019

(86) PCT No.: PCT/US2019/068786
§ 371 (c)(1),
(2) Date: Jun. 30, 2021

(87) PCT Pub. No.: WO2020/146155
PCT Pub. Date: Jul. 16, 2020

(65) Prior Publication Data
US 2022/0119402 A1    Apr. 21, 2022

Related U.S. Application Data

(60) Provisional application No. 62/790,862, filed on Jan. 10, 2019.

(51) Int. Cl.
*C07D 491/16* (2006.01)
*A61K 45/06* (2006.01)

(52) U.S. Cl.
CPC ............ *C07D 491/16* (2013.01); *A61K 45/06* (2013.01)

(58) Field of Classification Search
CPC .............................. C07D 491/16; A61K 45/06
See application file for complete search history.

(56) References Cited

U.S. PATENT DOCUMENTS 5,494,913 A    2/1996    Chu et al.

OTHER PUBLICATIONS

F. Annang et al.: "MDN-0185, an Antiplasmodial Polycyclic Xanthone Isolated from *Micromonospora* sp. CA-206353", Journal of Natural Products, vol. 81, Jun. 20, 2018 (Jun. 20, 2018), pp. 1687-1691, DOI: 10.1021 /acs.jnatprod.8b00323.
T. Bunyapaiboonsri et. al.: "Actinomadurone, a polycyclic tetrahydroxanthone from *Actinomadura* sp. BCC 35430", Tetrahedron Letters, vol. 58, Jul. 4, 2018 (Jul. 4, 2018), pp. 3223-3225, DOI: 10.1016/j.tetlet.2017.07.008.
Foreign Search Report on PCT PCT/US2019/068786 Dtd May 26, 2020.

*Primary Examiner* — Sun Jae Yoo
(74) *Attorney, Agent, or Firm* — Foley & Lardner LLP

(57) ABSTRACT

Turbinmicin, an isolated compound of Formula (I) or IA is provided. Turbinomycin compounds of Formula (II) or (IIA) are also provided. A compound isolated from a bacterial species from the sea squirt, *Ecteinascidia turbinate*, and having a chemical formula of $C_{34}H_{29}NO_{11}$ is also provided. Compositions including turbinmicin and turbinmicin compounds, such as pharmaceutical compositions including effective amounts of turbinmicin or turbinomicing compounds for treating fungal infections such as *Candida* and *Aspergillus*, including drug-resistant strains thereof, are also disclosed. Methods of treating fungal infections with turbinmicin, turbinmicin compounds and compositions thereof are disclosed.

21 Claims, 9 Drawing Sheets
Specification includes a Sequence Listing.

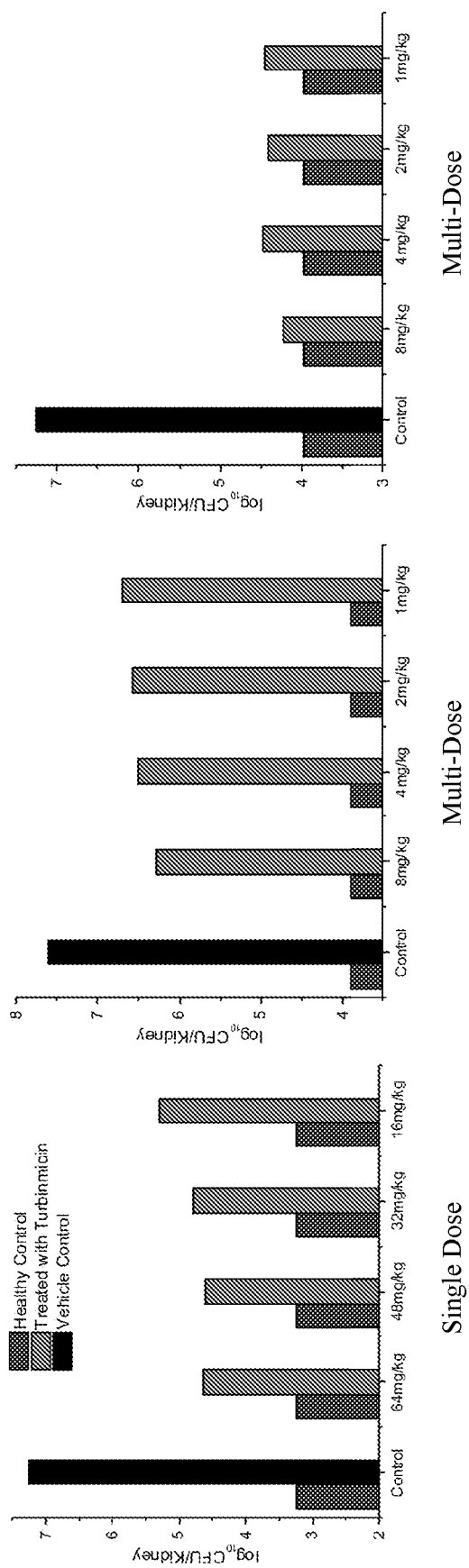
FIG. 7A  *C. albicans* K-1
FIG. 7B  *C. albicans* K-1
FIG. 7C  *C. auris* B11211

TURBINMICIN COMPOUNDS, COMPOSITIONS AND USES THEREOF

CROSS-REFERENCE TO RELATED PATENT APPLICATIONS

This application is a U.S. National Phase Application under 35 U.S.C. § 371 of International Application No. PCT/US2019/068786, filed Dec. 27, 2019, which claims the benefit of priority to U.S. Provisional Application No. 62/790,862, filed on Jan. 10, 2019, both of which are incorporated herein by reference in their entirety.

STATEMENT OF GOVERNMENT SUPPORT

This invention was made with government support under AI109673 and AI142720 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jun. 30, 2021, is named 032026-1469_SL.txt and is 1,555 bytes in size.

FIELD OF THE TECHNOLOGY

The present technology relates to a new compound called turbinmicin, compositions and methods of use thereof. The new isolated compound and compositions containing it are useful as antifungals, and show activity even against multi-drug resistant fungal infections.

BACKGROUND

More than 3-million patients worldwide are afflicted by fungal infections, and this number only continues to rise with increasing at-risk immunocompromised population. Today, only three antifungal drug classes are available for clinical use. The development of new antifungals has been hampered, in part, by the close evolutionary relationship between fungi and their human hosts. In addition to this paucity of drug options, many of the agents exhibit limited efficacy or toxic side-effects. Therefore, despite therapy, patient survival remains unacceptably low. In fact, fungi lead as the cause of infection-related mortality in many cancer and transplant populations. For example, the 90-day survival following a diagnosis of invasive *Candida* infection approaches 50%. The outcomes are even worse for patients with *Aspergillus* and other mold infections, with mortality reaching 80-90%. The prevalence of poor outcomes increase further with the recent emergence of pathogens that exhibit resistance to first-line antifungal options. For example, a recent global study of patients with *Aspergillus* pneumonia identified triazole-resistant *Aspergillus* sp. in nearly 50% of patients in high-risk groups. Similarly, the utility of echinocandins, first-line agents for treatment of invasive *Candida glabrata* infection, is currently limited by drug resistance in up to 15% of cases in some medical centers. Most recently, the multidrug resistant "killer fungus", *Candida auris*, has emerged and is spreading throughout healthcare facilities. In the United States, *C. auris* has prompted an urgent threat alert from the Centers for Disease Control and Prevention (CDC).

SUMMARY

A new compound, called turbinmicin has been discovered and isolated from *Micromonospora* sp. (strain WMMC415), a bacterial species isolated from the sea squirt, *Ecteinascidia turbinatae*. Turbinmicin has the chemical formula $C_{34}H_{29}NO_{11}$. Isolated turbinmicin has the structure of Formula I and includes stereoisomers thereof:

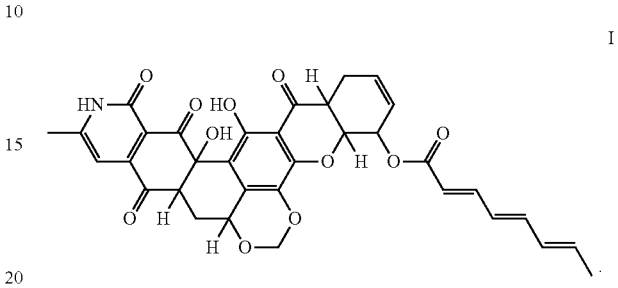

I

In any embodiments, turbinmicin has the stereochemistry and structure of Formula IA:

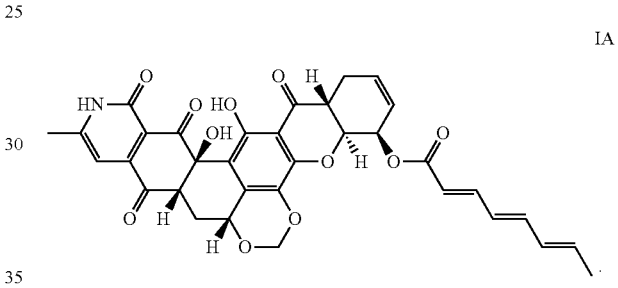

IA

Pharmaceutical compositions including turbinmicin and a pharmaceutically acceptable carrier are also provided. Methods of treating fungal infections by administering an effective amount of turbinmicin to a mammal in need thereof are disclosed.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3B, a $^{13}$C-$^{13}$C COSYLR spectrum of $^{13}$C labeled turbinmicin (125 MHz, CDCl$_3$/MeOD 1:1).

FIGS. 7A-C show graphs of in vivo single (7A) and multi-dose (7B, 7C) experiments with turbinmicin against *C. albicans* K-1 (7A, 7B) and *C. auris* B 11211 (7C) using a neutropenic, murine, disseminated candidiasis model. Single dose experiments required (16, 32, 48 and 64 mg/kg) of turbinmicin to be administered and animals then sacrificed at 6 h post drug administration. In multi-dose experiments, mice infected by *C. auris* B11211 or *C. albicans* K1 were treated with turbinmicin at 1, 2, 4, and 8 mg/kg by an intraperitoneal route every 8 h in 24 h.

DETAILED DESCRIPTION

Figure 1:
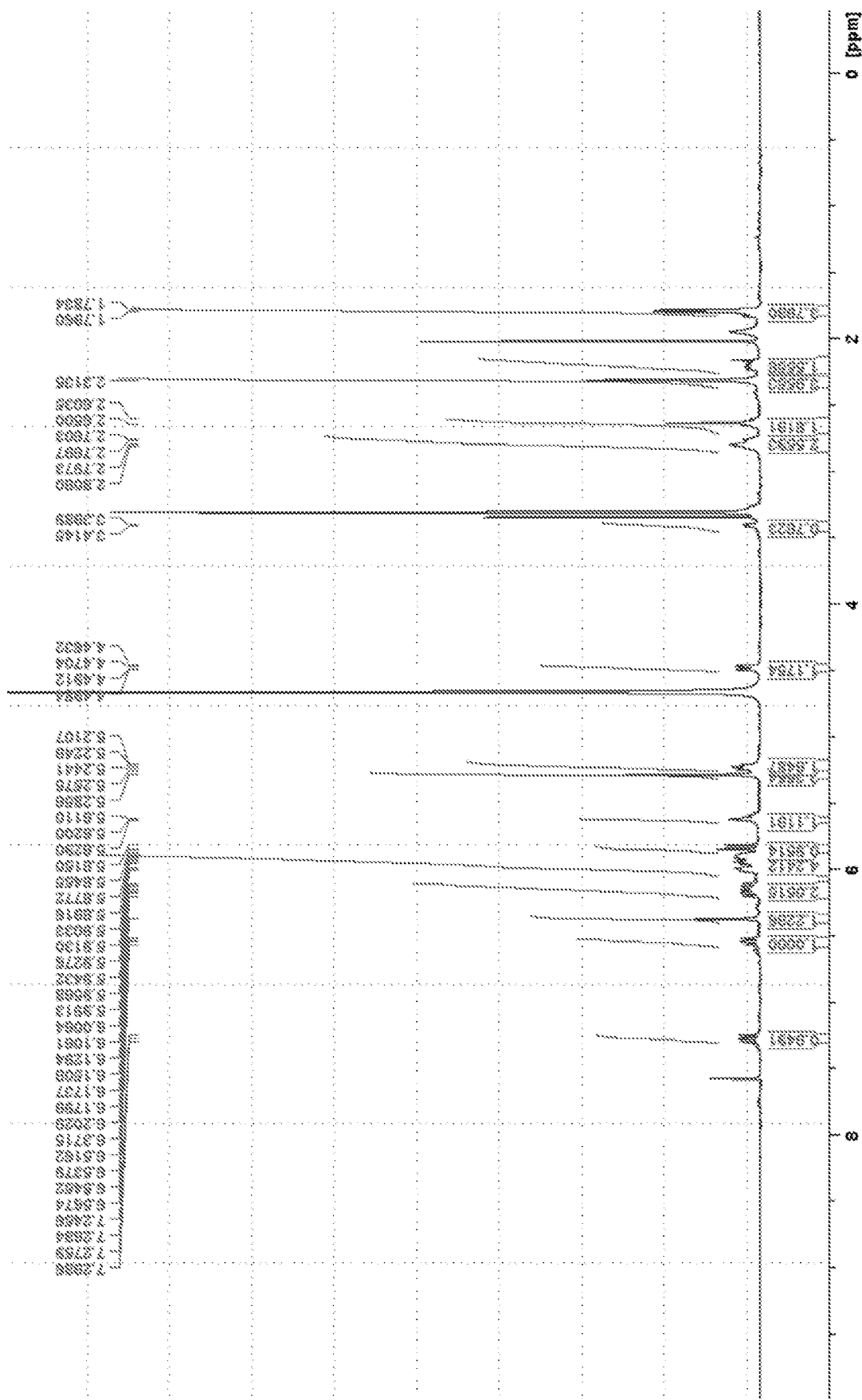
FIG. 1 shows a $^1$H NMR spectrum (500 MHz, CDCl$_3$/MeOD 1:1) for turbinmicin.
Figure 2:
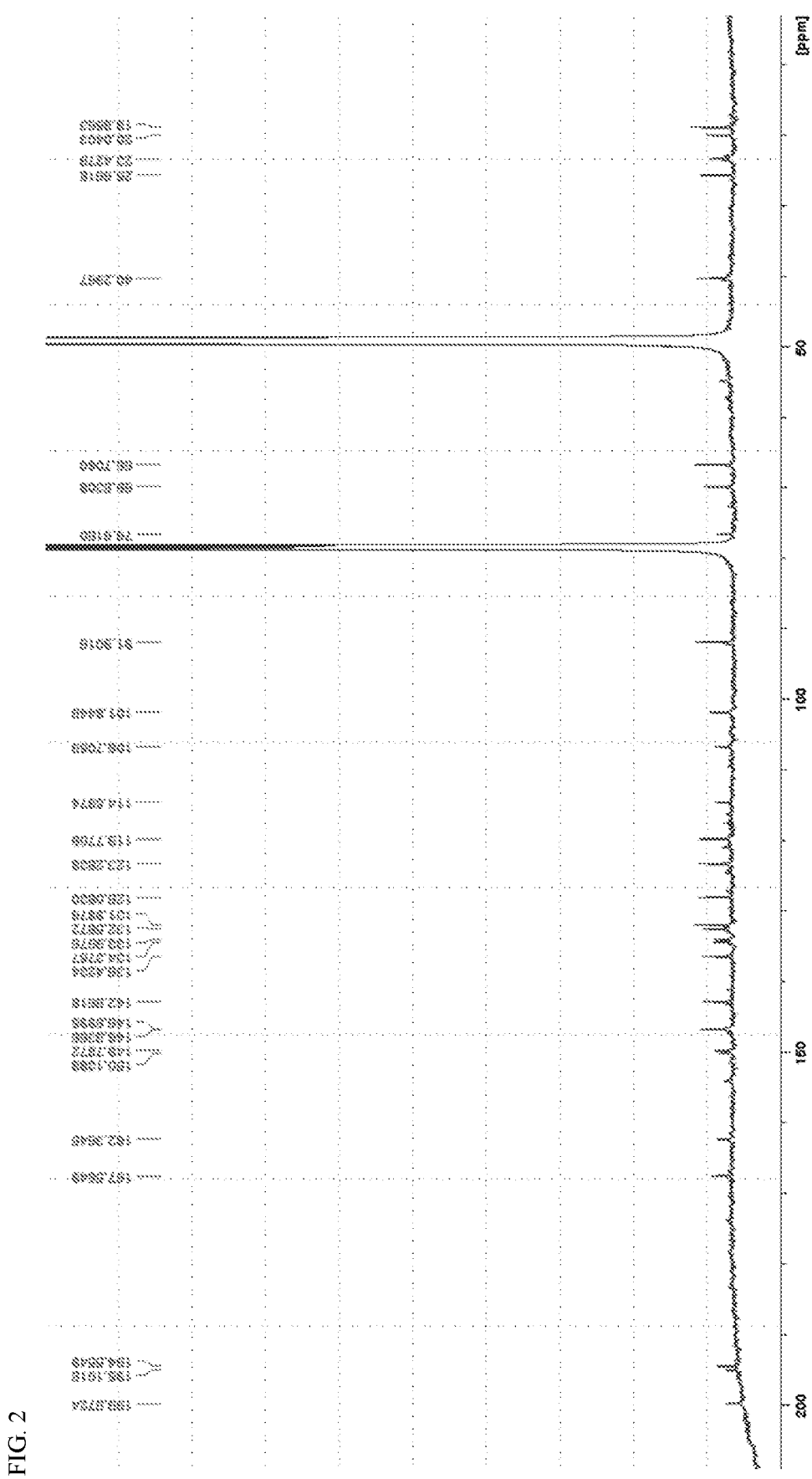
FIG. 2 shows a $^{13}$C NMR spectrum (125 MHz, CDCl$_3$/MeOD 1:1) for turbinmicin.

The present technology provides an isolated compound useful for the treatment of fungal infections, including multi-drug resistant fungal infections. Thus, in accordance with one aspect, the technology includes a compound isolated from *Micromonospora* sp. associated with the sea squirt, *Ecteinascidia turbinata*. The compound, called turbinmicin, represents a new class of antifungal compounds and in any embodiment of the present technology, has the structure shown by Formula I:

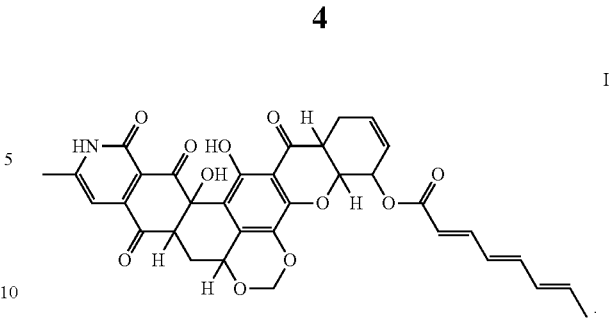

Isolated turbinmicin has a chemical formula $C_{34}H_{29}NO_{11}$ and exhibits any of the $^{13}C$ NMR peaks at or about the chemical shifts shown in Table 1, including 1, 2, 3, 4, 5, 6, 7, 8, 9, 10 or more thereof. For example, turbinmicin may exhibit 1, 2, 3, 4, 5, 6, 7, 8, 9, or 10 $^{13}C$ NMR peaks including those at or about the chemical shifts selected from the group consisting of 199.9, 195.1, 194.7, 167.7, 162.3, 154.2, 150.2, 149.8, 146.8, 146.7, 142.9, 136.5, 134.4, 134.0, 132.6, 130.0, 128.2, 123.3, 121.1, 119.8, 114.6, 106.8, 101.9, 91.9, 78.7, 76.6, 69.8, 66.8, 54.9, 40.4, 25.7, 23.4, 20.1 and 19.0 ppm. Similarly, isolated turbinmicin exhibits any of the $^1H$ NMR peaks at or about the chemical shifts shown in Table 1, including 1, 2, 3, 4, 5, 6, 7, 8, 9, 10 or more thereof. For example, turbinmicin may exhibit 1, 2, 3, 4, 5, 6, 7, 8, 9, or 10 $^1H$ NMR peaks selected from those at about 7.28, 6.55, 6.37, 6.19, 6.14, 6.01, 5.95, 5.90, 5.83, 5.63, 5.29, 5.23, 4.49, 3.41, 3.30, 2.81, 2.79, 2.64, 2.32, 2.21 and 1.79 ppm.

Turbinmicin may exhibit one, two, or three UV absorptions ($\lambda_{max}$) selected from those at about 241, 289 and 383 nm. The term "about" will be understood by those of skill in the art to include values within ±2% of the stated value, or in any embodiments, ±1% or even ±0.5% of the stated values.

TABLE 1

Summary of $^1H$ and $^{13}C$ NMR data for Turbinmicin (500 MHz for $^1H$, 125 MHz for $^{13}C$, CDCl$_3$/MeOD 1:1).

| Positon | $\delta_C$, mult. | $\delta_H$ (J in Hz) | $^1H$-$^1H$ COSY | HMBC$^a$ | $^{13}C$-$^{13}C$ COSY | $^{13}C$-$^{13}C$ COSYLR |
|---|---|---|---|---|---|---|
| 1 | 162.3, qC | | | | 15 | 3, 5, 14, 26 |
| 2 | 154.2, qC | | | | 3, 26 | |
| 3 | 101.9, CH | 6.37, s | | 2, 5, 15, 26 | 2, 4 | |
| 4 | 146.7, qC | | | | 3, 5 | |
| 5 | 194.7, qC | | | | 4, 6 | 1 |
| 6 | 54.9, CH | 3.41, m | | | 5, 7, 13 | |
| 7 | 23.4, CH$_2$ | 2.64, m; 2.81, m | 8 | 5, 6, 8 | 6, 8 | 9 |
| 8 | 69.8, CH | 5.23, dd | 7 | 7, 9, 11, 12, 16 | 7, 11 | 9 |
| 9 | 91.9, CH$_2$ | 5.29, s | | 8, 11 | | 7, 8, 10, 11 |
| 10 | 149.8, qC | | | | 11, 18 | 8, 9, 12, 19 |
| 11 | 134.0, qC | | | | 8, 10 | 9 |
| 12 | 114.6, qC | | | | 13, 16 | |
| 13 | 76.6, qC | | | | 6, 12, 14 | |
| 14 | 195.1, qC | | | | 13, 15 | 1 |
| 15 | 121,1, qC | | | | 1, 14 | |
| 16 | 150.2, qC | | | | 12, 17 | |
| 17 | 106.8, qC | | | | 16, 25 | 24 |
| 18 | 134.4, qC | | | | 10, 17 | |
| 19 | 78.7, CH | 4.49, dd (3.6, 14) | 20, 24 | 20, 23, 24, 25 | 20, 24 | 10, 22, 27 |
| 20 | 66.8, CH | 5.63, t (4.5) | 19, 21 | 19, 21, 22, 24, 27 | 19, 21 | 23, 25, 27 |
| 21 | 123.3, CH | 5.90, m | 20, 22 | 19, 20, 23 | 20, 22 | |
| 22 | 132.6, CH | 6.01, m | 21, 23 | 20, 23, 24 | 21, 23 | 19, 25 |
| 23 | 25.7, CH$_2$ | 2.21, m; 2.79, m | 22, 24 | 19, 21, 22, 24 | 22, 24 | 20, 25 |
| 24 | 40.4, CH | 3.30, m | 19, 23 | 19, 20, 23,25 | 19, 23, 25 | 17, 21 |
| 25 | 199.9, qC | | | | 17, 24 | 19, 20, 22, 23 |
| 26 | 20.1, CH$_3$ | 2.32, s | 2, 3 | 2 | 1, 3 | |
| 27 | 167.7, qC | | | | 28 | 19, 20, 29, 30 |
| 28 | 119.8, CH | 5.83, d (15.0) | 29 | 27, 30 | 27, 29 | 31 |
| 29 | 146.8, CH | 7.28, dd (15.0, 11.5) | 28, 30 | 27, 28, 30, 31 | 28, 30 | 32 |
| 30 | 128.2, CH | 6.19, dd (11.5, 14.8) | 29, 31 | 28, 29, 32 | 29, 31 | 27, 33 |

TABLE 1-continued

Summary of $^1$H and $^{13}$C NMR data for Turbinmicin (500 MHz for $^1$H, 125 MHz for $^{13}$C, CDCl$_3$/MeOD 1:1).

| Positon | $\delta_C$, mult. | $\delta_H$ (J in Hz) | $^1$H-$^1$H COSY | HMBC[a] | $^{13}$C-$^{13}$C COSY | $^{13}$C-$^{13}$C COSYLR |
|---|---|---|---|---|---|---|
| 31 | 142.9, CH | 6.55, dd (11.7, 14.8) | 30, 32 | 29, 32, 33 | 30, 32 | 28, 34 |
| 32 | 132.0, CH | 6.14, dd (11.7, 14.6) | 31, 33 | 30, 31, 34 | 31, 33 | 29 |
| 33 | 136.5, CH | 5.95, dt (6.3, 14.6) | 32, 34 | 31, 32, 34 | 32, 34 | 30 |
| 34 | 19.0, CH$_3$ | 1.79, d (6.3) | 33 | 31, 32, 33 | 33 | 31 |

[a]HMBC correlations are from proton(s) to the indicated carbon.

In any embodiment described herein, a compound of Formula I may be the diastereomer shown below (Formula IA). The numbering of the compound is as indicated below, and such numbering is referred to herein.

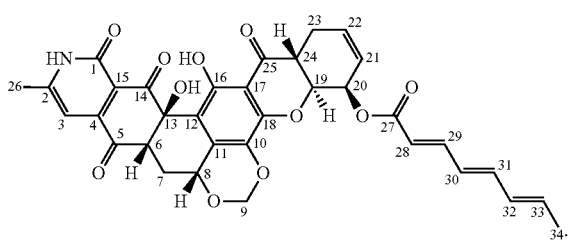

IA

In another aspect, the present technology provides analog of turbinmicin, such as compounds of Formula II or a stereoisomer thereof,

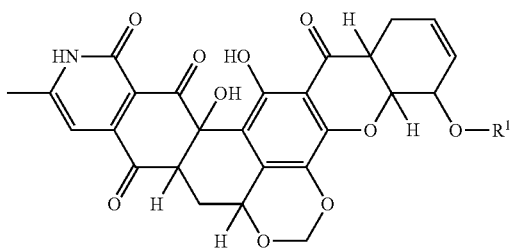

II wherein
R$^1$ is H or C(O)—R$^2$, and
R$^2$ is a substituted or unsubstituted alkyl or alkenyl group.
In any embodiments, the compound of Formula II has the structure of Formula IIA:

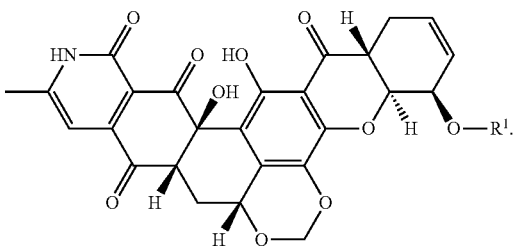

IIA

In any embodiments of compounds of Formula II (or IIA), or methods of making or using such compounds, R$^1$ is not 1-oxo-oct-2,4,6-trienyl. In any embodiments, R$^1$ is C(O)—R$^2$. In any embodiments, R$^2$ is an unsubstituted alkyl group. In any embodiments, R$^2$ is an unsubstituted C$_{5-9}$ alkyl group. Compounds of Formula II (or IIA) may be readily made by transesterifying under standard conditions the oxo-octyl-trienyl group with other saturated and unsaturated carboxylic acids, including but not limited to formic acid, acetic acid, propionic acid, butanoic acid, but-2-enoic acid, etc.

The compounds described herein may be isolated at various purities, e.g., a purity of at least 60 wt %, at least 70 wt %, at least 80 wt %, at least 90 wt %, at least 95 wt %, at least 96, at least 97 wt %, at least 98 wt %, at least 99 wt % or at least 99.5 wt %.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

Stereoisomers of compounds (also known as optical isomers) include all chiral, diastereomeric, and racemic forms of a structure, unless the specific stereochemistry is expressly indicated. Thus, compounds disclosed herein include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

In another aspect the present technology provides a pharmaceutical composition including turbinmicin as described herein and a pharmaceutically acceptable carrier. The pharmaceutical compositions of any embodiment herein may be formulated for oral, parenteral, nasal, topical administration or any of the routes discussed herein. In any embodiment herein, the pharmaceutical composition may include an effective amount of a compound of any embodiment of the present technology. The effective amount may be an effective amount for treating a fungal infection, including those caused by any of the fungi disclosed herein. In any embodiments, the effective amount of compound may be an effective amount for treating any infection due to drug-resistant fungi, including those disclosed herein (see below).

In some embodiments, the pharmaceutical composition comprises turbinmicin and a pharmaceutically acceptable carrier comprising aqueous DMSO, e.g., DMSO in water, DMSO in 0.9% saline or DMSO in phosphate buffered saline (e.g., about 0.01 to about 0.1 molar Na/K phosphate buffer, about pH 7.4). In some embodiments the amount of DMSO in aqueous solution varies from at least about 1% by weight to about 80% by weight. For example, the pharmaceutically acceptable carrier may be at or about 1 wt %, 2 wt %, 5 wt %, 10 wt %, 15 wt %, 20 wt %, 30 wt %, 40 wt %, 50 wt %, 60 wt %, 70 wt %, 80 wt % DMSO in aqueous solution (e.g., water, saline, PBS or the like) or an amount within a range between and including any two of the foregoing values such as about 1 wt % to about 70 wt %, about 2 wt % to about 60 wt %, about 10 wt % to about 50 wt % or about 60 wt %, or about 5 wt % to about 20 or 30 wt %, or about 2 wt % to about 15 wt % or about 20 wt % DMSO in aqueous solution. Using a carrier such as aqueous DMSO, turbinmicin's limited water solubility (<0.5 mg/mL) may be increased to greater than 0.5 mg/mL to 10 mg/mL, e.g., to 1, 2, 3, 4, 5, 6, 7, 8, 9, or even 10 mg/mL, or a range between and including any two of the foregoing values in the aqueous pharmaceutical formulation. For example, in some such formulations, the range of turbinmicin may be from greater than 0.5 mg/mL to about 3 mg/mL or to about 5 mg/mL or from about 1 mg/mL to about 2, 3 or 4 mg/mL.

The present technology provides methods of treating a fungal infection comprising administering an effective amount of turbinmicin, or a pharmaceutical composition as described herein to a mammal in need thereof. The mammal may be, e.g., a human, primate (e.g. monkey, chimpanzee, ape), cat, dog, pig, mouse, rat, horse, sheep, among others. In any embodiment described herein, the mammal may be human. The infection may occur, e.g., in the skin, mouth, pharynx, esophagus, toenails, fingernails, urogenital tract, or lungs, or may be systemic, in, e.g., immunocompromised patients. In any embodiment of the present methods, the fungal infection may be caused by one or both of *Candida, Fusarium, Scedosporium, Rhizopus, Mucor, Apophysomyces, Lichteimia, Cynninghamella*, or *Aspergillus*. In any embodiments of the present methods, the fungal infection may be caused by *Aspergillus*, such as *Aspergillus fumigatus*, or it may be caused by *Candida*, e.g., *Candida albicans, Candida auris, Candida enolase, Candida tropicalis, Candida glabrata, Candida krusei, Candida parapsilosis, Candida stellatoidea, Candida parakawsei, Candida lusitaniae, Candida pseudotropicalis*, and *Candida guilliermondi*. In any embodiments of the present methods, the fungal infection may be caused by *Candida albicans, Candida glabrata, Candida auris, Candida tropicalis, Rhizopus delemar, Mucor circinelloides, Apophysomyces elegans, Lichteimia corymbiferea, Aspergillus fumigatus*, and drug-resistant strains thereof. In any embodiment described herein, the fungal infection may be caused by one or more of drug-resistant fungi, such as, but not limited to, *Aspergillus fumigatus* (e.g., 11628), *Candidas albicans, Candida glabrata* (e.g., 4720), *Candida auris* (e.g., B11211). Similarly, the compounds and compositions described herein may be used for therapy, such as for treatment of fungal infections such as any of those described herein, or for use in the manufacture of a medicament for any such treatments.

In another aspect, the present technology provides pharmaceutical compositions of turbinmicin with a second antifungal agent (or combination of agents) different from turbinmicin, including but not limited to azoles, echinocandins, or polyenes, as well as methods of using the same. Antifungal agents include drugs which demonstrate clinical benefit in treatment of fungal infections in a mammal, including a human. Suitable second antifungal agents include but are not limited to one or more of amphotericin B, flucytosine, fluconazole, isavuconazole, micafungin, voriconazole, posaconazole and forazoline. In any embodiment described herein, an effective amount of a compound as described herein (e.g., turbinmicin), a salt thereof or a pharmaceutical composition comprising the compound and a pharmaceutically acceptable carrier, may be administered to a mammal in need thereof, wherein the second antifungal agent(s) is/are administered to the mammal in need thereof simultaneously, sequentially or separately with a compound as described herein, or any embodiment of the pharmaceutical composition as describe herein.

"Treating" within the context of the instant technology, means alleviation, in whole or in part, of symptoms associated with a disorder or disease, or slowing, inhibition or halting of further progression or worsening of those symptoms, or prevention or prophylaxis of the disease or disorder in a subject at risk for developing the disease or disorder. For example, within the context of treating fungal infections, successful treatment may include reduction or eradication of the pathogenic fungus, from the body; clinical benefit; an alleviation of symptoms, such as a reduction or elimination of rash, itching, chafing, burning, throat thrush, redness, soreness, fever, cough, night sweats, weight loss, wheezing, and shortness of breath.

As used herein, an "effective amount" of a compound of the present technology refers to an amount of the compound that alleviates, in whole or in part, symptoms associated with a disorder or disease, or slows or halts of further progression or worsening of those symptoms, or prevents or provides prophylaxis for the disease or disorder in a subject at risk for developing the disease or disorder. Those skilled in the art are readily able to determine an effective amount. For example, one way of assessing an effective amount for a particular disease state is by simply administering a compound of the present technology to a patient in increasing amounts until progression of the disease state is decreased or stopped or reversed. An "effective amount" of a compound of the present technology also refers to an amount of the compound that, for example, reduces a population of fungi where the fungal population may be outside a subject (e.g., in a media in a container).

The instant technology also provides for compositions and medicaments including a compound disclosed herein and a pharmaceutically acceptable carrier. Such compositions may be prepared by mixing one or more compounds of the present technology, pharmaceutically acceptable salts thereof or stereoisomers thereof, with pharmaceutically acceptable carriers, excipients, binders, diluents or the like to treat fungal infections. The compounds and compositions of the present technology may be used to prepare formulations and medicaments that treat a variety of fungal infections, e.g., *Candida* and *Aspergillus* as disclosed herein. Such compositions can be in the form of, for example, granules, powders, tablets, capsules, creams, ointments, syrup, suppositories, injections, emulsions, elixirs, suspensions or solutions. The instant compositions can be formulated for various routes of administration, for example, by oral, parenteral, topical, injection, rectal, nasal, vaginal, or via implanted reservoir. Parenteral or systemic administration includes, but is not limited to, subcutaneous, intravenous, intraperitoneally, intramuscular, intrathecal, intracranial, and intracerebroventricular injections. The following dosage forms are given by way of example and should not be construed as limiting the instant technology.

For oral, buccal, and sublingual administration, powders, suspensions, granules, tablets, pills, capsules, gelcaps, and caplets are acceptable as solid dosage forms. These can be prepared, for example, by mixing one or more compounds disclosed herein, or pharmaceutically acceptable salts or stereoisomers thereof, with at least one additive such as a starch or other additive. Suitable additives are sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. Optionally, oral dosage forms can contain other ingredients to aid in administration, such as an inactive diluent, or lubricants such as magnesium stearate, or preservatives such as paraben or sorbic acid, or anti-oxidants such as ascorbic acid, tocopherol or cysteine, a disintegrating agent, binders, thickeners, buffers, sweeteners, flavoring agents or perfuming agents. Tablets and pills may be further treated with suitable coating materials known in the art.

Liquid dosage forms for oral administration may be in the form of pharmaceutically acceptable emulsions, syrups, elixirs, suspensions, and solutions, which may contain an inactive diluent, such as water. Pharmaceutical formulations and medicaments may be prepared as liquid suspensions or solutions using a sterile liquid, such as, but not limited to, an oil, water, an alcohol, and combinations of these. Pharmaceutically suitable surfactants, suspending agents, emulsifying agents, may be added for oral or parenteral administration.

As noted above, suspensions may include oils. Such oils include, but are not limited to, peanut oil, sesame oil, cottonseed oil, corn oil and olive oil. Suspension preparation may also contain esters of fatty acids such as ethyl oleate, isopropyl myristate, fatty acid glycerides and acetylated fatty acid glycerides. Suspension formulations may include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water may also be used in suspension formulations.

Injectable dosage forms generally include aqueous suspensions or oil suspensions, which may be prepared using a suitable dispersant or wetting agent and a suspending agent. Injectable forms may be in solution phase or in the form of a suspension, which is prepared with a solvent or diluent. Acceptable solvents or vehicles include sterilized water, Ringer's solution, or an isotonic aqueous saline solution. Alternatively, sterile oils may be employed as solvents or suspending agents. Typically, the oil or fatty acid is non-volatile, including natural or synthetic oils, fatty acids, mono-, di- or tri-glycerides.

For injection, the pharmaceutical formulation and/or medicament may be a powder suitable for reconstitution with an appropriate solution as described above. Examples of these include, but are not limited to, freeze dried, rotary dried or spray dried powders, amorphous powders, granules, precipitates, or particulates. For injection, the formulations may optionally contain stabilizers, pH modifiers, surfactants, bioavailability modifiers and combinations of these.

Compounds of the present technology also may be formulated as a composition for topical administration (e.g., vaginal cream). These formulations may contain various excipients known to those skilled in the art. Suitable excipients may include, but are not limited to, cetyl esters wax, cetyl alcohol, white wax, glyceryl monostearate, propylene glycol monostearate, methyl stearate, benzyl alcohol, sodium lauryl sulfate, glycerin, mineral oil, water, carbomer, ethyl alcohol, acrylate adhesives, polyisobutylene adhesives, and silicone adhesives.

The composition may be in the form of a vaginal cream containing the composition of matter as set forth herein present in a nonliquefying base. The nonliquefying base may contain various inactive ingredients such as, for example, cetyl esters wax, cetyl alcohol, white wax, glyceryl monostearate, propylene glycol monostearate, methyl stearate, benzyl alcohol, sodium lauryl sulfate, glycerin, and mineral oil. Such composition may be formulated similar to PREMARIN® Vaginal Cream made commercially available by Wyeth-Ayerst Laboratories.

Dosage units for rectal administration may be prepared in the form of suppositories which may contain the composition of matter in a mixture with a neutral fat base, or they may be prepared in the form of gelatin-rectal capsules which contain the active substance in a mixture with a vegetable oil or paraffin oil.

Compounds of the present technology may be administered to the lungs by inhalation through the nose or mouth. Suitable pharmaceutical formulations for inhalation include solutions, sprays, dry powders, or aerosols containing any appropriate solvents and optionally other compounds such as, but not limited to, stabilizers, antimicrobial agents, antioxidants, pH modifiers, surfactants, bioavailability modifiers and combinations of these. Formulations for inhalation administration contain as excipients, for example, lactose, polyoxyethylene-9-lauryl ether, glycocholate and deoxycholate. Aqueous and nonaqueous aerosols are typically used for delivery of inventive compounds by inhalation.

Ordinarily, an aqueous aerosol is made by formulating an aqueous solution or suspension of the compound together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins such as serum albumin, sorbitan esters, oleic acid, lecithin, amino acids such as glycine, buffers, salts, sugars or sugar alcohols. Aerosols generally are prepared from isotonic solutions. A nonaqueous suspension (e.g., in a fluorocarbon propellant) can also be used to deliver compounds of the present technology.

Aerosols containing compounds for use according to the present technology are conveniently delivered using an inhaler, atomizer, pressurized pack or a nebulizer and a suitable propellant, e.g., without limitation, pressurized dichlorodifluoromethane, trichlorofluoromethane, dichlorotetrafluoroethane, nitrogen, air, or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch. Delivery of aerosols of the present technology using sonic nebulizers is advantageous because nebulizers minimize exposure of the agent to shear, which can result in degradation of the compound.

For nasal administration, the pharmaceutical formulations and medicaments may be a spray, nasal drops or aerosol containing an appropriate solvent(s) and optionally other compounds such as, but not limited to, stabilizers, antimicrobial agents, antioxidants, pH modifiers, surfactants, bioavailability modifiers and combinations of these. For administration in the form of nasal drops, the compounds may be formulated in oily solutions or as a gel. For administration of nasal aerosol, any suitable propellant may be used including compressed air, nitrogen, carbon dioxide, or a hydrocarbon based low boiling solvent.

Besides those representative dosage forms described above, pharmaceutically acceptable excipients and carriers are generally known to those skilled in the art and are thus included in the instant present technology. Such excipients and carriers are described, for example, in "Remingtons Pharmaceutical Sciences" Mack Pub. Co., New Jersey (1991), which is incorporated herein by reference.

The formulations of the present technology may be designed to be short-acting, fast-releasing, long-acting, and sustained-releasing as described below. Thus, the pharmaceutical formulations may also be formulated for controlled release or for slow release.

The instant compositions may also comprise, for example, micelles or liposomes, or some other encapsulated form, or may be administered in an extended release form to provide a prolonged storage and/or delivery effect. Therefore, the pharmaceutical formulations and medicaments may be compressed into pellets or cylinders and implanted intramuscularly or subcutaneously as depot injections or as implants such as stents. Such implants may employ known inert materials such as silicones and biodegradable polymers.

Specific dosages may be adjusted depending on conditions of disease, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant technology.

A therapeutically effective amount of a compound of the present technology may vary depending upon the route of administration and dosage form. Effective amounts of such compounds typically fall in the range of about 0.01 up to about 100 mg/kg/day, or about 0.05 to about 50 mg/kg/day, and more typically in the range of about 0.1 up to 5 mg/kg/day. Typically, the compound or compounds of the instant technology are selected to provide a formulation that exhibits a high therapeutic index. The therapeutic index is the dose ratio between toxic and therapeutic effects and can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology is further illustrated by the following examples, which should not be construed as limiting in any way.

EXAMPLES

General Experimental Procedures

Melting points were measured on an OpiMelt automated melting point apparatus and were uncorrected. Optical rotations were measured on a PerkinElmer 241 polarimeter. UV spectra were recorded using an Aminco/OLIS UV-vis spectrophotometer. IR spectra were measured with a Bruker Equinox 55/S FT-IR spectrophotometer. NMR spectra were obtained in MeOD/CDCl$_3$ with a Bruker Avance 500 MHz spectrometer equipped with a $^1$H{$^{13}$C/$^{15}$N} cryoprobe and a Bruker Avance 500 MHz spectrometer equipped with a $^{13}$C/$^{15}$N{$^1$H} cryoprobe. HRMS data were acquired with a Bruker MaXis 4G QTOF mass spectrometer.

Example 1: Isolation of Turbinmicin from *Ecteinascidia turbinate*

Marine Natural Product Screening Libraries Platform. We used a combination of hierarchal clustering analysis and principal component analysis (57, 58) for strains prioritization. We used fermentation in two distinct media (ASW-A and RAM2) for each prioritized strain followed by extraction, fractionation, and finally HPLC purification (80 fractions/strain) directly into 96-well plates. Next, in vitro high-throughput screening was applied to these HPLC purified fractions using a four-point dose response in 384 well plates with an Echo acoustic droplet delivery system against *Candida albicans* K1. Primary hits were defined as active against *Candida albicans* K1. The primary hits were further evaluated by analytical methods including 1.7 mm NMR and HRESIMS. Hits that produced known molecules were deprioritized, and we prioritized hits that demonstrated potentially new scaffolds. Moreover, the new antifungal agents were evaluated by in vivo studies and preliminary mechanism of action studies.

Biological Material. Ascidians specimens were collected in August 2014 from the Florida Keys (24° 39.490', −81° 25.217'). A voucher specimen for *Ecteinascidia turbinata* (Herdman, 1880) is housed at the University of Wisconsin-Madison. For cultivation, a sample of ascidian (1 cm$^3$) was rinsed with sterile seawater, macerated using a sterile pestle in a micro-centrifuge tube, and dilutions were made in sterile seawater, with vortexing between steps to separate bacteria from heavier tissues. Dilutions were separately plated on three media: ISP2, R2A, and M4. Each medium was supplemented with 50 µg/mL cycloheximide and 25 µg/mL nalidixic acid. Plates were incubated at 28° C. for at least 28 days, and strain WMMC 415 was purified from a R2A isolation plate.

Sequencing. Genomic DNA was extracted using the UltraClean Microbial DNA Isolation kit (Mo Bio Laboratories, Inc.). 16S rDNA genes were amplified using 100-200 ng genomic DNA template with the primers 8-27F (5' to 3' GAGTTTGATCCTGGCTCAG (SEQ ID NO: 1)) and 1492R (5' to 3' GGTTACCTTGTTACGACTT (SEQ ID NO: 2)). The following PCR conditions were used: 94° C. for 5 min, followed by 30 cycles of 94° C. for 30 s, 55° C. for 1 min, 72° C. for 1.5 min, with a final step of 72° C. for 5 min. The PCR bands were excised from the gel and purified using the QIAquick Gel Extraction kit (QIAGEN). One µL purified product was sequenced. Sequencing reactions were performed by the UW Biotechnology Center and reactions were sequenced with an ABI 3730xl DNA Analyzer. WMMC 415 were identified as *Micromonospora* sp. by 16S sequencing, and demonstrated 100% sequence similarity to a *Micromonospora* sp. (accession number KC856927).

Media for Study of $^{13}$C Incorporation. ASW-A medium: 20 g soluble starch, 10 g U$^{13}$C-glucose, 5 g peptone, 5 g yeast extract, 5 g CaCO$_3$ per liter of artificial seawater. Ram2 medium: 4 g corn meal, 15 g maltose, 10 g U$^{13}$C-glucose, 7.5 g pharmamedia, 5 g yeast per liter of 50% artificial sea water. Modified RAM2 medium: 4 g corn meal, 25 g U$^{13}$C-glucose, 7.5 g pharmamedia, 5 g yeast per liter of 50% artificial sea water.

Fermentation, Extraction, and Isolation. For making artificial seawater, solution I (415.2 g NaCl, 69.54 g Na$_2$SO$_4$, 11.74 g KCl, 3.40 g NaHCO$_3$, 1.7 g KBr, 0.45 g H$_3$BO$_3$, 0.054 g NaF) and II (187.9 g MgCl$_2$·6H$_2$O, 22.72 g CaCl$_2$·2H$_2$O, 0.428 SrCl$_2$·6H$_2$O) were made up separately, and combined to give a total volume of 20 L. Two 10 mL seed cultures (25×150 min tubes) in medium ASW-A (20 g soluble starch, 10 g glucose, 5 g peptone, 5 g yeast extract, 5 g CaCO$_3$ per liter of artificial seawater) were inoculated with strain WMMC415 and shaken (200 RPM, 28° C.) for 14 days. Two-liter flasks (2×500 mL) containing Ram2 medium (4 g corn meal, 10 g glucose, 15 g maltose, 7.5 g pharmamedia, 5 g yeast per liter of 50% artificial seawater) with Diaion HP20 (7% by weight) were inoculated with 10 mL from the culture tube and shaken at 200 rpm at 28° C. for fourteen days. Filtered HP20 was washed with water and extracted with acetone. The acetone extract (3.5 g) was subjected to liquid-liquid partitioning using 30% aqueous MeOH and CHCl$_3$ (1:1). The CHCl$_3$-soluble partition (1.5 g) was fractionated by Sephadex LH20 column chromatography (column size CHCl$_3$: MeOH, 1:1) Fractions containing turbinmicin were subjected to RP HPLC (50%/50% to 95%/5% MeOH/H$_2$O with H$_2$O containing 0.1% acetic acid over 30 min, 20 mL/min, followed by 95/5% to 100% of MeOH/H$_2$O for 1 min, and a hold at 100%/0% of MeOH for 10 min, 20 mL/min) using a Phenomenex Gemini C$_{18}$ column (250×30 mm, 5 μm), yielding 1 (140 mg, t$_R$ 27.1 min). For $^{13}$C incorporation, the same procedure was used (1×100 mL) with labeled modified Ram2 media, yielding 7.0 mg of $^{13}$C labeled turbinmicin (U$^{13}$C-glucose substituted for unlabeled glucose).

Example 2: Structure Elucidation

Analytical data were gathered for turbinmicin, including UV, IR, HRMS, single-crystal X-ray diffraction, and $^1$H, $^{13}$C and 2D NMR spectra.

Figure 3A:
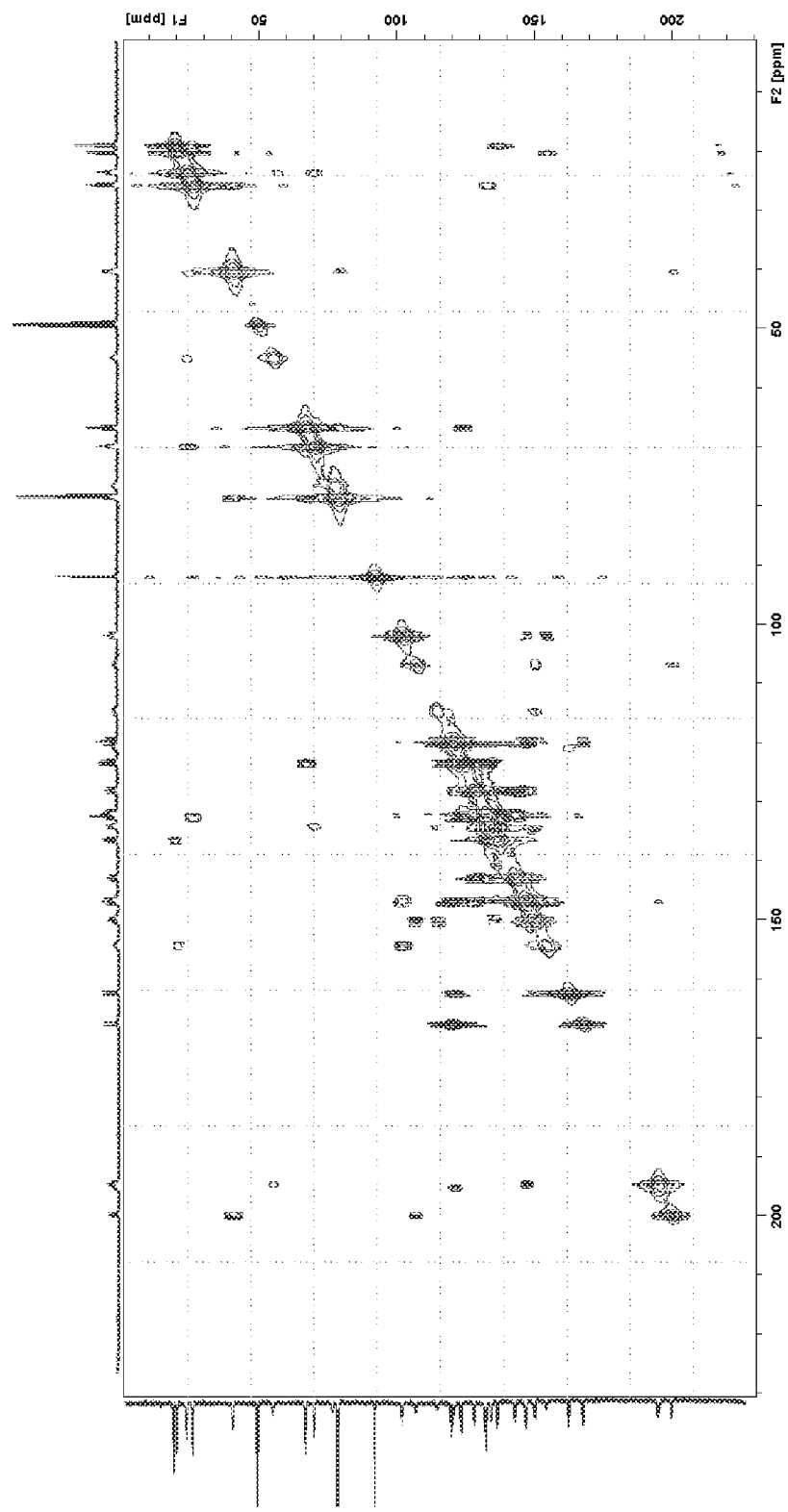
FIGS. 3A and 3B shows 2D NMR spectra for turbinmicin including FIG. 3A a $^{13}$C-$^{13}$C COSY spectrum of $^{13}$C labeled turbinmicin (125 MHz, CDCl$_3$/MeOD 1:1).
Figure 3B:
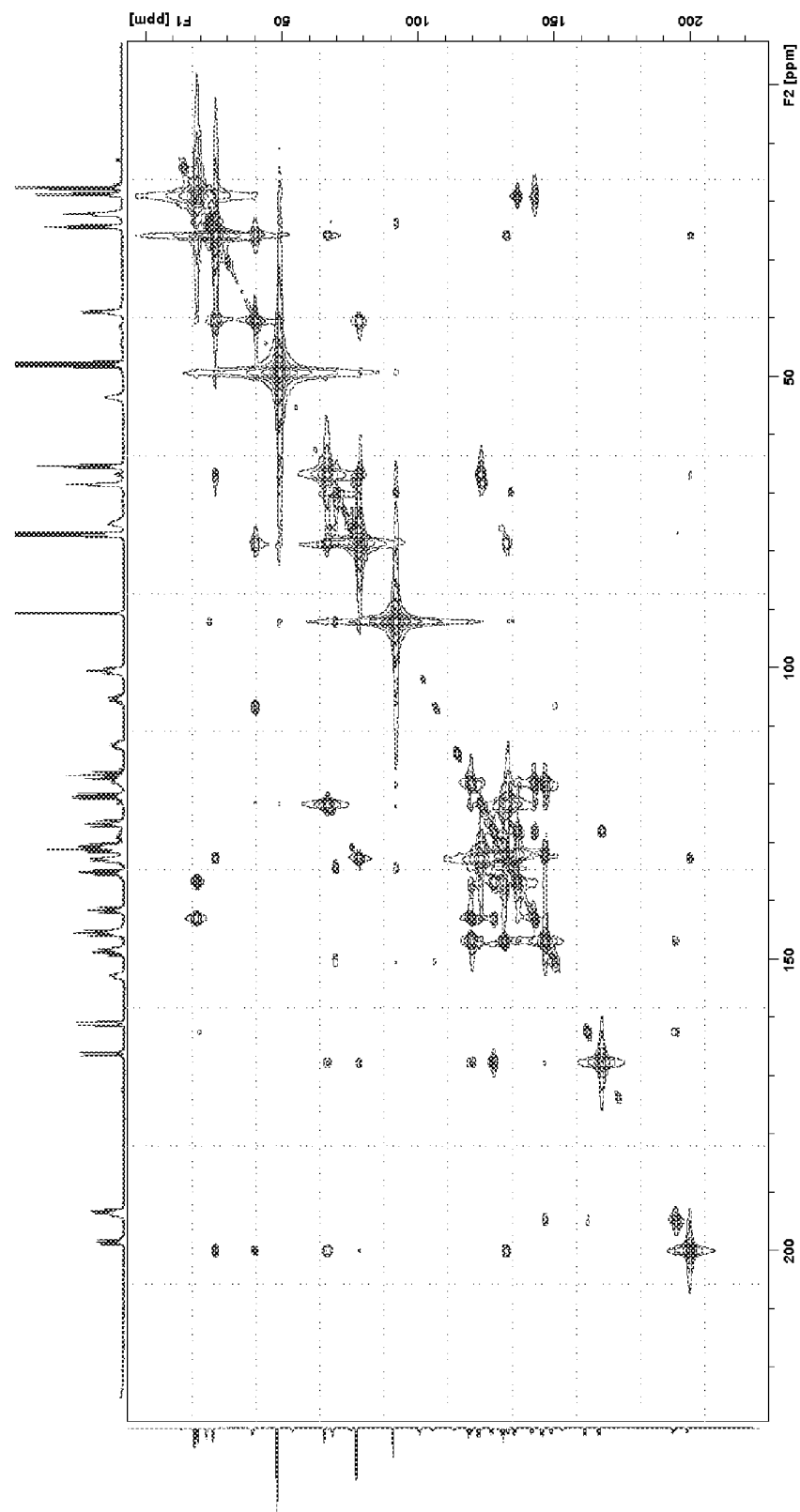
Figure 4:
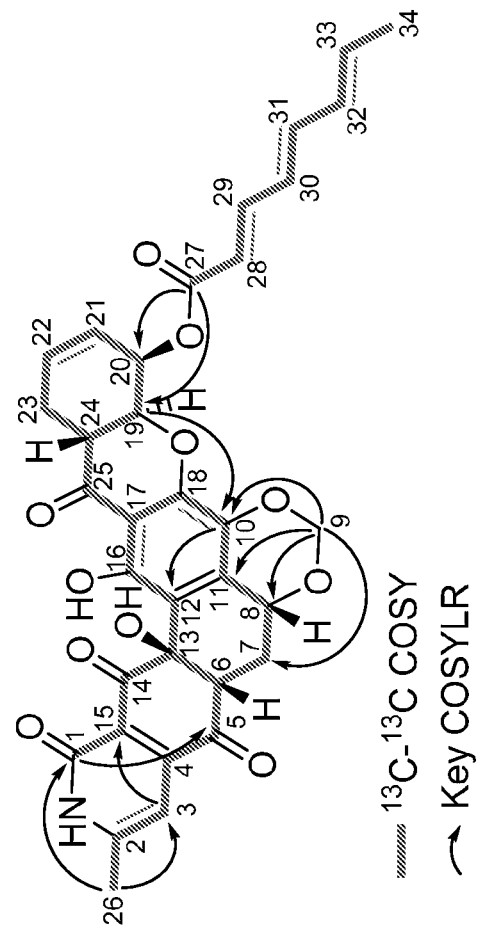
FIG. 4 is a schematic drawing showing how $^{13}$C-$^{13}$C COSY and COSYLR data established all carbon connectivities.
Figure 5:
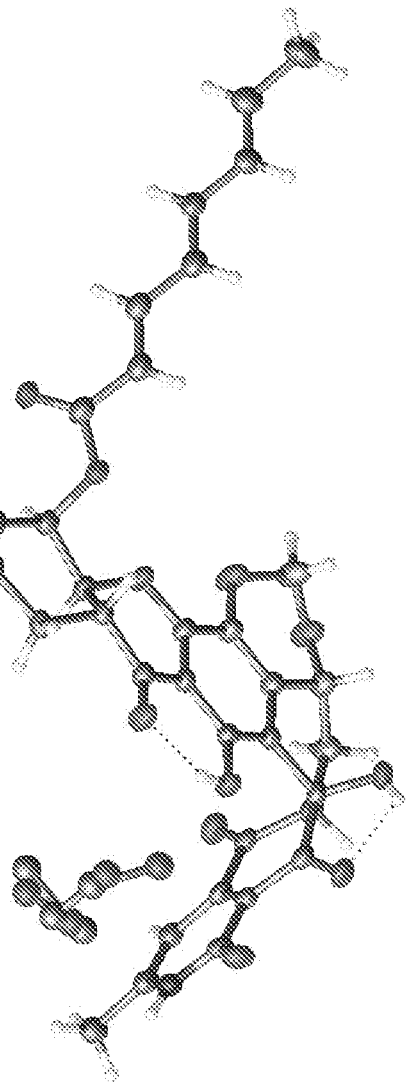
FIG. 5 is an ORTEP drawing of the single crystal structure of turbinmicin.

Turbinmicin was obtained as a yellow solid with a molecular formula of C$_{34}$H$_{29}$NO$_{11}$ as determined by the HRESIMS ([M+H]$^+$ m/z 628.1809, calcd. 628.1813 for C34H$_{30}$NO$_{11}$) and harboring 21 degrees of unsaturation. Interpretation of $^1$H, $^{13}$C and HSQC NMR spectral data were vital to structure elucidation efforts for turbinmicin as were 2D NMR methods such as COSY, ROESY, NOESY, HSQC, and HMBC. $^{13}$C-labeled turbinmicin generated by fermentation using uniformly-labeled $^{13}$C glucose, and acquisition of $^{13}$C-$^{13}$C COSY (1-bond correlations) enabled an established approach to solving similarly challenging structures (see Supporting Information). Optimally, 79% $^{13}$C incorporation into turbinmicin was realized using Ram2 fermentation medium and subsequent $^{13}$C-$^{13}$C COSY experiments revealed most of the carbon connectivities (FIG. 3A, FIG. 4). However, additional data were necessary to complete the planar structure of turbinmicin due to the presence of heteroatoms within specific carbon-carbon chains. The resultant substructures were connected together using $^{13}$C-$^{13}$C COSYLR data (FIG. 3B). In the $^{13}$C-$^{13}$C COSYLR spectrum, correlations from C-26 to C-1 and C-3 indicated that C-1 and C-3 were linked by a heteroatom. Considering the chemical shift of the C-2 olefinic carbon (δ$_C$ 154.2), and by comparison to a similar unit (δ$_C$ 152.8) in xantholipin, the nitrogen atom present in 1 was shown to be attached to C-1 and C-3, since the chemical shift of C-2 would be a little downfield if it was attached to an oxygen (δ$_C$ 162.7). Correlations between C-3 and C-15, and between C-1 and C-5 connected C-4 to C-15. $^{13}$C-$^{13}$C COSYLR correlations from C-9 to C-8, C-10 and C-11 suggested the presence of a 1,3-dioxane ring, while the correlation between C-10 and C-12 indicated that C-11 was attached to C-12. Further correlations observed between C-19 and C-10 revealed the presence of the 4-chromanone moiety which were typically found in xanthones. On the basis of the large vicinal $^1$H-$^1$H coupling constants (J=14.6-15.0 Hz), the alkene configurations were assigned as 28E, 30E, 32E. Correlations from C-27 to C-19 and C-20 indicated the ester was attached to C-20. Therefore, three exchangeable protons were required to satisfy the molecular formula of turbinmicin, including two hydroxy groups attached to C-13 and C-16, and an NH located at C-2, completing the planar structure. Having elucidated the planar structure of turbinmicin we next applied X-ray diffraction experiments using Cu K$_α$ (λ=1.54178 Å) radiation to solve the turbinmicin crystal structure (FIG. 5). These efforts, yielding the structure shown above unequivocally established the absolute configuration of turbinmicin as 6S, 8R, 13R, 19R, 20R, 24R.

X-ray Crystallographic Analysis of Turbinmicin. Crystallization from MeOH/H$_2$O/acetic acid (9:1:0.001) using the vapor diffusion method yield yellow crystals of turbinmicin. A yellow crystal with approximate dimensions 0.09×0.08× 0.01 mm$^3$ was selected under oil under ambient conditions and attached to the tip of a MiTeGen MicroMount©. The crystal was mounted in a stream of cold nitrogen at 100(1) K and centered in the X-ray beam by using a video camera. The crystal evaluation and data collection were performed on a Bruker D8 VENTURE diffractometer equipped with a Photon 100 detector with Cu K$_α$ (λ=1.54178 Å) radiation and the diffractometer to crystal distance of 3.50 cm (64). The initial cell constants were obtained from one φ scan with short exposure times. The reflections were successfully indexed by an automated indexing routine built in the APEXII program suite. The final cell constants were calculated from a set of 9863 strong reflections from the actual data collection. The data were collected by using the full sphere data collection routine to survey the reciprocal space to the extent of a full sphere to a resolution of 0.80 Å. A total of 32345 data were harvested by collecting 23 sets of frames with 0.6° scans in ω and φ with exposure times of 10-20 sec per frame. These highly redundant datasets were corrected for Lorentz and polarization effects. The absorption correction was based on fitting a function to the empirical transmission surface as sampled by multiple equivalent measurements (65). The systematic absences in the diffraction data were consistent for the space groups C2, Cm, and C2/m, but only the non-centrosymmetric space group C2 yielded chemically reasonable and computationally stable results of refinement (66-71). A successful solution by the direct methods provided most non-hydrogen atoms from the E-map. The remaining non-hydrogen atoms were located in an alternating series of least-squares cycles and difference Fourier maps. All non-hydrogen atoms were refined with anisotropic displacement coefficients. All hydrogen atoms were included in the structure factor calculation at idealized positions and were allowed to ride on the neighboring atoms with relative isotropic displacement coefficients. There is also one molecule of solvate methanol in the asymmetric unit. This molecules is severely disordered. It was modelled as disordered over four positions in a 40.6(4):25.1(3):21.5 (4):12.8(4) ratio. These molecules were refined with restraints and constrains. It was not possible to assign H atoms at reasonable positions to these molecules. The final least-squares refinement of 448 parameters against 6190 data resulted in residuals R (based on F$^2$ for I≥2σ) and wR (based on F$^2$ for all data) of 0.0387 and 0.1089, respectively. The final difference Fourier map was featureless. Crystal data for C$_{35}$H$_{33}$NO$_{12}$ (M=659.62 g/mol): monoclinic, space group C2 (no. 5), a=29.1822(6) Å, b=5.48042(12) Å, c=19.2762(4) Å, β=99.1077(9)°, V=3043.98(12) Å$^3$, Z=4, T=99.99 K, μ(Cu Kα)=0.918 mm$^{-1}$, D$_{calc}$=1.439 g/cm$^3$, 32345 reflections measured (4.642°≤2θ≤149.054°), 6190 unique (R$_{int}$=0.0260, R$_{sigma}$=0.0189), which were used in all calculations. The final R$_1$ was 0.0387 (I>2σ(I)) and wR$_2$ was 0.1089 (all data).

Historically, "heavy atoms" such as Br and Cl were considered as necessary prerequisites for such studies, since a "heavy" atom has a strong resonant scattering signal whereas light atoms have weak signals. Resonant scattering signals are stronger for radiation sources with longer wavelength, thus Cu radiation is preferred to Mo radiation. Nowadays the combination of strong X-ray sources, sensitive detectors and fast data collections allows to collect a lot of redundant data fast and determine absolute configuration even for light-atom molecules with weak anomalous dispersion signal. In the case of compound 1, the signal was weak but strong enough to produce a conclusive result of the absolute configuration due to enough oxygen atoms present in the molecule, Turbinmicin (1): yellow needles; mp 255-257° C.; [α]$^{25}_D$-438 (c 0.1, MeOH/CHCl$_3$ 1:1); UV (MeOH) λ$_{max}$ (log ε) 241 (4.18) nm, 289 (4.40) nm, 383 (4.03) nm; IR (ATR) υ$_{max}$ 3385, 1764, 1673, 1538, 1434, 1380, 1202, 1135, 1050, 1026, 840, 802, 722, 669 cm$^{-1}$; $^1$H and $^{13}$C NMR (See Table 1); HRESIMS [M+H]$^+$ m/z 628.1809 (calcd for C$_{34}$H$_{30}$NO$_{11}$, 628.1813).

Example 3: In Vitro Biological Activity

Hemolysis Assay. Assays were performed in 384-well plates using sheep blood (0.1% triton as the positive control). Sheep's blood (Ward's Science) was washed with PBS and diluted to a concentration of 6×10$^7$ red blood cells per ml. A volume of 50 μL of blood was incubated with compound for 1 h, and subsequently pelleted at 4000 rpm for 10 min. Thirty microliters of supernatant were transferred to a clear plate and OD570 was read. An increase in OD indicated the red blood cell lysis and hemolytic activity. Turbinmicin concentrations exceeding the MIC by 1000-fold did not exhibit red blood cell toxicity, suggesting a wide therapeutic window for this compound.

In vitro MIC susceptibility testing. Turbinmicin was tested for antifungal activity against five Candida isolates, C. albicans K-1, C. tropicalis 98-234, C. auris B 11211, and C. glabrata 4720, and C. albicans SN 250, and MICs were determined using a broth microdilution method for yeasts. 1 was dissolved in DMSO, serially diluted to 10 concentrations (0.125-64 μg/mL), and tested in a 96-well plate in RPMI medium. Amphotericin B was used as a positive control and the MICs range were 0.25-1.5 μg/mL. Six untreated media controls were included on each plate. The plates were incubated at 33° C. for 72 h. The MICs were determined as the lowest concentration that inhibited visible growth. The MICs were read at 24, 48, and 72 hours, respectively. Turbinmicin was also test for antifungal activity against A. fumigatus F11628 in a similar manner, and the dose range was 8-0.016 mg/L. Isavuconazole and posaconazole were used as the positive controls and the MICs are 8 μg/mL. Results are shown in Tables 2 and 3 for turbinimicin activity against various fungi, including drug-resistant fungi.

Notably, C. auris B11211, a clinical isolate from India, is highly multidrug-resistant to the three classes of antifungal drugs in current clinical use including fluconazole, micafungin and amphotericin B. A. fumigatus is the most common etiological agent of aspergillosis, and azoles represent first-line therapy for all forms of aspergillosis and comprise the only class of drug available orally. Overall the reported frequency of azole resistance in A. fumigatus is approximately 2%, and A. fumigatus F11628 is a pan-azole pathogen. Both C. auris and A. fumigatus are associated with high morbidity and mortality underscoring the important potential of turbinmicin as an antifungal candidate.

TABLE 2

| Strain | Drug Resistance Phenotype | Turbinmicin MIC (ug/mL) |
|---|---|---|
| Aspergillus fumigatus 11628 | Triazole | 0.03 |
| Candida glabrata 4720 | Echinocandin | 0.5 |
| Candida albicans K-1 | | 0.25 |
| Candida tropicalis 98-234 | | 0.5 |
| Candida auris B11211 | Amphotericin B, fluconazole, micafungin | 0.25 |

TABLE 3

| Species | Strain | MIC (ug/mL) Turbinmicin | Fluconzole | Amphotericin B | Posaconazole | Micafungin | Genotype |
|---|---|---|---|---|---|---|---|
| C. albicans | K1 | 0.25 | 0.5 | 0.25 | 0.03 | 0.03 | |
| | SN250 | 0.25 | | | | | |
| | 580 | 0.5 | 4 | | 0.06 | 0.016 | |
| | 98-210 | 0.25 | 16 | | 0.12 | 0.03 | |
| | 98-17 | 0.25 | 16 | 0.25 | 0.12 | 0.06 | |
| C. glabrata | 4720 | 0.5 | | | | 4 | Fks2_HS1_S645P |
| | 729 | 0.5 | | | | 8 | Fks2_HS1_S663P |
| | 14378 | 0.5 | | | | 2 | Fks1_HS1_S629P |
| | 5592 | 0.5 | | | | 0.016 | |
| | 513 | 0.5 | | | | 0.016 | |
| C. tropicalis | 98-234 | 0.5 | 32 | | 0.125 | | |
| | 2597 | 0.25 | | | | | |
| | ATCC 750 | 0.25 | | | | | |
| | 1751 | 0.25 | | | | | |
| | 001 | 0.5 | | | | | |
| C. auris | B11804 | 0.5 | 2 | 0.5 | 0.03 | 0.5 | |
| | B11220 | 0.125 | 4 | 0.38 | 0.06 | 0.12 | |
| | B11221 | 0.5 | 128 | 0.38 | 0.5 | 1 | |
| | B11801 | 0.5 | 16 | 6 | 0.12 | 1 | |
| | B11203 | 0.5 | 256 | 4 | 0.12 | 0.25 | |
| | B11219 | 0.25 | >256 | 3 | 0.5 | 4 | |

TABLE 3-continued

| Species | Strain | Turbinmicin | Fluconzole | Amphotericin B | Posaconazole | Micafungin | Genotype |
|---|---|---|---|---|---|---|---|
| | B11211 | 0.25 | >256 | 1.5 | 0.5 | 4 | |
| | B11104 | 0.5 | >256 | 1 | 0.5 | 0.25 | |
| | B11799 | 0.5 | 16 | 0.5 | 0.06 | 2 | |
| | B11785 | 0.25 | 8 | 1.5 | 0.016 | 0.5 | |
| Aspergillus fumigatus | F11628 | 0.03 | | | 8 | | Cyp51 G138C |
| | 293 | 0.125 | | | 0.5 | | |
| | F16216 | 0.25 | | | 2 | | Cyp51 L98H + TR |
| | F14532 | 0.25 | | | 1 | | Cyp51 M220T |
| | F14403 | 0.25 | | | 8 | | Cyp51 G54R |
| Fusarium spp. | | 0.125 | | | | | |
| | | 0.5 | | | | | |
| Scedosporium spp. | | 0.5 | | | | | |
| Rhizopus delemar | | 4.0 | | | | | |
| Rhizopus oryzae | | >8.0 | | | | | |
| Mucor circinelloides | | 4.0 | | | | | |
| Apophysomyces elegans | | 4.0 | | | | | |
| Lichteimia corymbiferea | | 4.0 | | | | | |
| Cynninghamella bertholletiae | | >8.0 | | | | | |

Figure 6A:
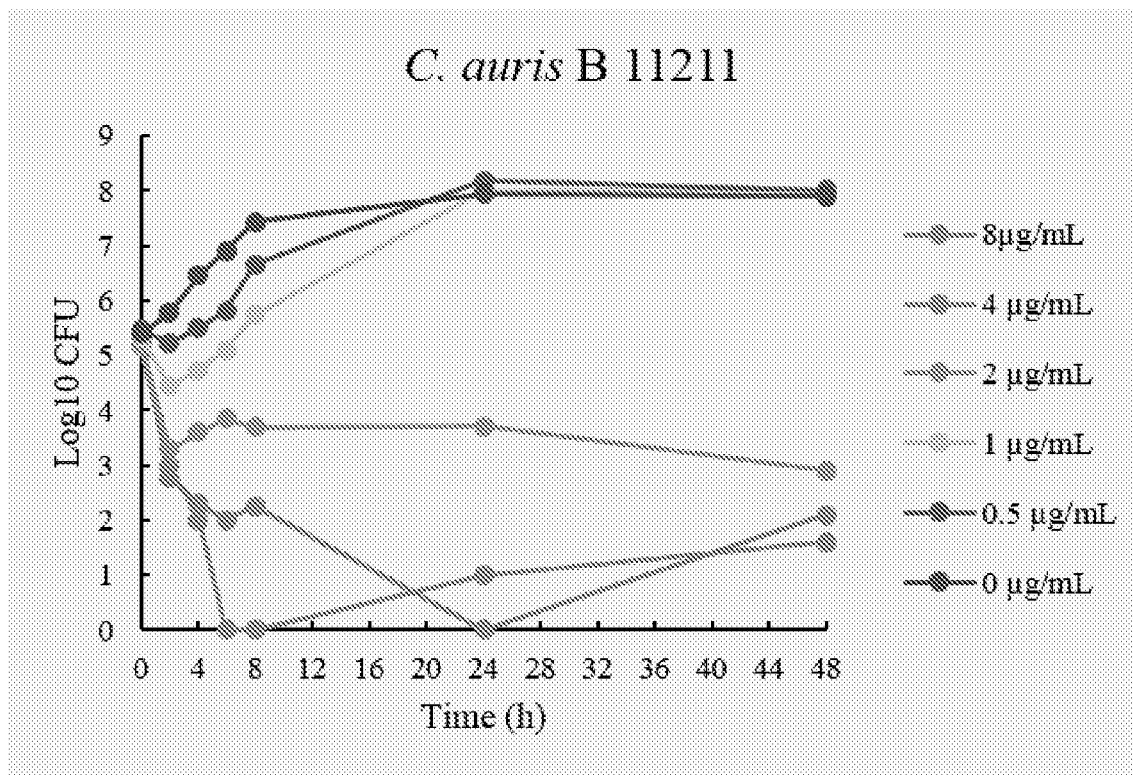
FIGS. 6A-C show time-kill curves for turbinmicin against (6A) *C. auris* B11211, (6B) *C. albicans* K-1, and (6C) *C. glabrata* 4720. Kill curves were generated from data collected at 0, 2, 3, 4, 8, 24, and 48 hours after exposure of indicated fungal colony culture to turbinmicin at concentrations spanning 1× to 16×MIC (i.e., at 0, 0.5, 1, 2, 4 and 8 µg/mL turbinmicin).
Figure 6B:
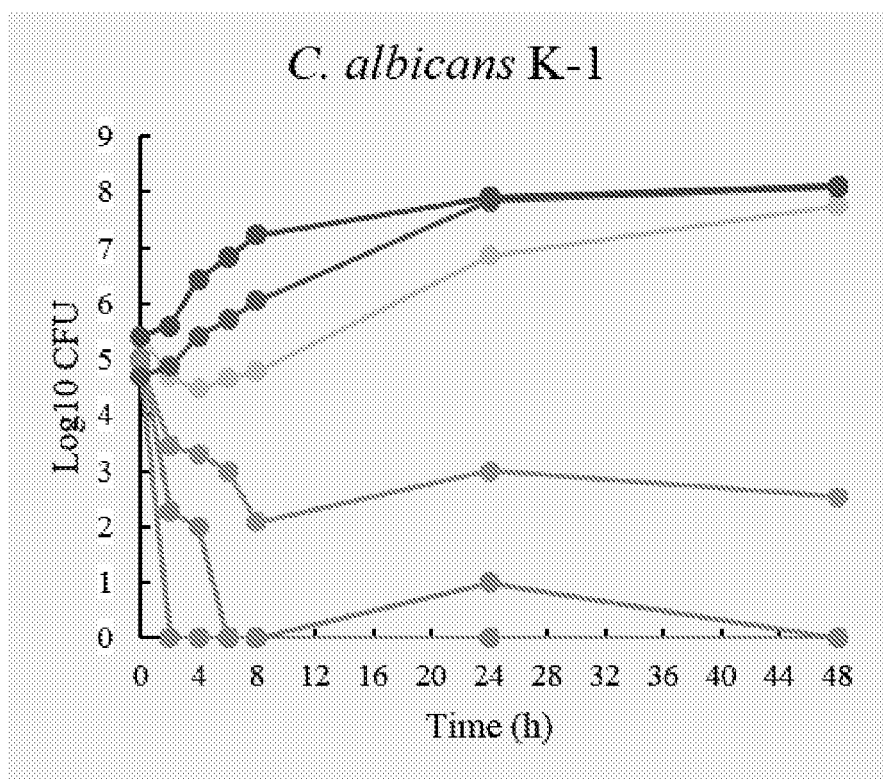
Figure 6C:
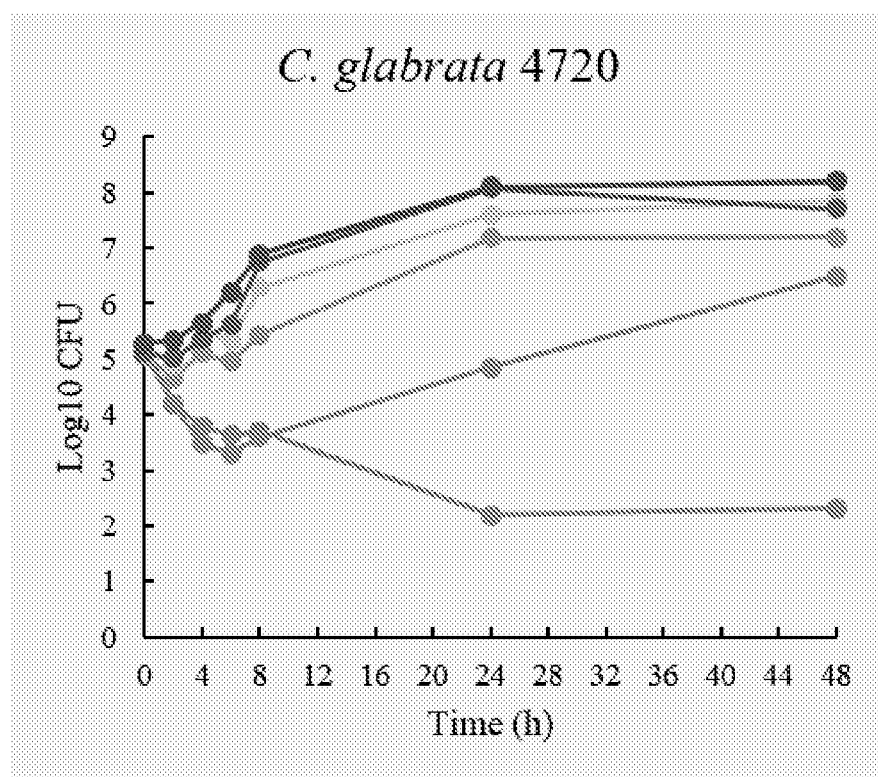

Time Kill Experiments. Fresh *Candida* colonies from an overnight growth were added to normal saline and the turbidity was adjusted to a 0.6 transmittance at 530 nm to provide a standard suspension ($1*10^6$ CFU/mL). This suspension was diluted with RPMI 1640 medium buffered with MOPS and a standard compound stock solution to achieve a starting inoculum of approximately $10^5$ CFU/ml. Each 20 mL culture (RPMI 1640 medium buffered with MOPS) was incubated at 35° C. with constant shaking, and 0.1 mL samples were withdrawn for the determination of fungal counts at 0, 2, 4, 6, 8, 24 and 48 h. Colony counts were determined by viable counts on sabouraud agar plate (SDA) after incubation for 48 h. Growth control for each organism were prepared without antifungal and run in parallel. Fungacidal activity was observed as shown in FIGS. 6A-6C against *C. auris, C. albicans*, and *A. fumigatus*.

Organisms, Biofilm formation, drug treatment and XTT assay. The processors were performed as previously described.[12] The strains used for this study included *C. albicans* strains K-1 and SN250, *C. auris* strains B11804 and B11211, and *A. fumigatus* strains F11628. Biofilms were formed in 96-well polystyrene plates. Cells were enumerated with a hemocytometer and were resuspended in RPMI-MOPS at a concentration of $10^6$/mL. To each well of a 96-well microtiter plate, 100 μL of inoculum was added. After 6 or 24 h (6 h for *C. albicans* and *C. auris*; 24 h for *A. fumigatus* strains) of incubation at 37° C., biofilms were gently washed twice with phosphate-buffered saline (PBS). Dilutions of antifungal agents or biocides and fresh RPMI-MOPS in a total volume of 200 μL were added to biofilms for 6 and 24 h (*C. albicans* and *C. auris*) or 24 h (*A. fumigatus* strains) of incubation at 37° C. For a subset of assays, after 24 h of drug treatment, biofilms were washed with PBS, and drug dilutions were added for an additional 24 h of incubation. The concentrations studied were from 250 to 1 μg/mL. After the drug treatment and incubation period, an XTT reduction assay was performed as a measure of metabolic activity in order to estimate the burden of viable cells. XTT and phenazine methosulfate stock solutions were prepared fresh for each set of assays and were kept away from light. XTT products from BioVectra, Biotium, MP Biomedicals, and Sigma were included. The solutions were centrifuged to remove any insoluble material prior to use. Phenazine methosulfate was dissolved in water (0.32 mg/mL). After drug dilutions were removed from each well, the biofilms were gently washed twice with PBS. To each well, 90 μL XTT and 10 μL phenazine methosulfate were added. The plates were incubated in the dark at 37° C. for 40 min (*C. albicans* and *C. auris* strains) or 2.5 h (*A. fumigatus* strains). Absorbances at 492 nm were recorded using an automated plate reader.

SEM of *C. albicans* SN250. Sample preparation for SEM was performed on biofilm samples formed on a coverslip after 24 h incubation of a 1-mL inoculum containing $1\times10^6$ cells/mL in serum buffered RPMI-1640 medium containing no drug and 2.5, 10 and 40 μg/ml of Turbinmicin. Growth controls without any treatment were included. Direct visualization of *C. albicans* SN250 biofilm morphology revealed a dense, filamentous growth with little yeast forms present in growth control, however the filamentous growth was inhibited dramatically at 40 μg/mL, with many yeast forms present. We also observed pits on the cell surface, which suggests a potential structural defect in the cell surface of *C. albicans* SN250.

Example 4: In Vivo Biological Activity

As turbinmicin had limited aqueous solubility, various solubilizing conditions (Table 4) were tested. Only mixtures of DMSO and water were found to solubilize turbinmicin at concentrations greater than 0.5 mg/mL.

TABLE 4

| No. | Aqueous Solvent | Highest Turbmicin conc. Achieved (mg/mL) |
|---|---|---|
| 1 | PBS | ≤0.5 |
| 2 | DMSO (1% in PBS) | ≤0.5 |
| 3 | DMSO (5% in PBS) | ≤1 |
| 4 | DMSO (10% in PBS) | 2 |
| 5 | PEG 400 (50% in PBS) | ≤0.5 |
| 6 | Kolliphor EL (10% in PBS) | ≤0.5 |
| 7 | Tween 80 (2% in PBS) | ≤0.5 |

Animals. Six-week-old ICR Swiss specific-pathogen-free female mice weighing 23 to 27 g were used for all studies. Animals were maintained in accordance with the American Association for Accreditation of Laboratory Care criteria. Animal studies were approved by the University of Wisconsin Animal Research Committee.

*C. auris* B11211 and *C. albicans* K1 Infection model. A neutropenic, murine, disseminated candidiasis model was used for the treatment studies. Mice were rendered neutropenic (neutrophils, <100/mm³) by injecting them with cyclophosphamide (Mead Johnson Pharmaceuticals, Evansville, IN) subcutaneously 4 days (150 mg/kg) and 1 day (100 mg/kg) before infection, and 2 days after infection (100 mg/kg). Previous studies have shown neutropenia (<100 mm³) in this model for the 96-h study period.

*C auris* B11211 was subcultured on SDA 24 h prior to infection. Inoculum was prepared by placing three to five colonies into 5 ml of sterile pyrogen-free 0.9% saline warmed to 35° C. The final inoculum was adjusted to a 0.6 transmittance at 530 nm. Fungal counts of the inoculum determined by viable counts of *C. auris* on SDA were 6.25±0.03 $\log_{10}$ CFU ml⁻¹, respectively. Disseminated infection with the *Candida* was achieved by injection of 0.1 ml of inoculum via the lateral tail vein 2 h prior to the start of drug therapy. Treatment period was 24 h. Animals were sacrificed by $CO_2$ asphyxiation. Kidneys of each mouse were removed and placed in sterile 0.9% saline at 4° C. The homogenate was serially diluted and aliquots were plated on SDA for viable fungal colony counts after incubation for 24 h at 35° C. The lower limit of detection was 100 CFU ml-1. Results were expressed as the mean number of CFU per kidney for three mice. Control growth in untreated control mice was 7.7±0.11 $\log_{10}$ CFU/kidney.

*A. fumigatus* F11628 Infection model. Mice were rendered neutropenic (polymorphonuclear cells<100/mm³) by injection of 150 mg/kg of body weight cyclophosphamide subcutaneously (s.c.) on days −4, −1, and +3. Prior studies have shown this to sustain neutropenia for the 4-day experiment. Additionally, cortisone acetate (250 mg/kg given s.c.) was administered on day −1. Throughout the 4-day neutropenic period, mice were also given ceftazidime, 50 mg/kg/day s.c., to prevent opportunistic bacterial infection. Uninfected animals given the above immune suppression and antibiotic had 100% survival to study endpoint.

*A. fumigatus* F11628 (triazole resistant CYP51 G138C) was prepared by subculturing on potatoe-dextrose agar (PDA) 5 days prior to infection and incubated at 37° C. On the day of infection, the inoculum was prepared by flooding the culture plate with 5 ml of normal saline with 0.05% Tween 20. Gentle agitation was applied to release the conidia into the fluid. The conidial suspension was collected and quantitated by using a hemacytometer (Bright-Line; Hausser Scientific, Horsham PA). The suspension was diluted to a final concentration of $1 \times 10^7$ to $2 \times 10^7$ conidia/mL. Viability was confirmed by plating the suspension on PDA and determining CFU.

Infection was produced in animals using a nasal aspiration pneumonia model. Mice were anesthetized with a combination of ketamine and xylazine. Fifty microliters of a $1 \times 10^7$ to $2 \times 10^7$ conidial suspension was pipetted into the anterior nares and aspirated into the lungs. The procedure produced invasive aspergillosis in more than 90% of animals and 100% mortality in untreated infected mice by day 3 or 4.

Pulmonary fungal burden was determined by real-time quantitative PCR (qPCR). Briefly, at the time of sacrifice for moribund animals or at the end of therapy (4 days), lungs were aseptically removed and placed in a 2-ounce sterile polyethylene Whirl-Pak bag (Nasco, Fort Atkinson, WI) containing 2 mL of sterile saline (0.9%). Homogenization of lung tissue occurred in two steps. First, the lungs were manually homogenized using direct pressure to yield a primary homogenate. One milliliter of the primary homogenate was then transferred to a sterile 2-ml screw-cap microcentrifuge tube (Sarstedt, Newton, NC) with 700 µl of 425- to 600-µm acid-washed glass beads (Sigma-Aldrich, St. Louis, MO). The primary homogenate was mechanically disrupted by vigorous agitation in a BioSpec Mini-Bead-Beater (Bartlesville, OK) for 90 s at 4,200 rpm to yield a secondary homogenate. This secondary homogenate was stored at −20° C. until DNA extraction.

One hundred microliters of the secondary homogenate was mixed with 100 µL of buffer ATL (Qiagen, Valencia, CA) and 20 µL of proteinase K (Qiagen, Valencia, CA) and incubated overnight at 56° C. with gentle agitation. DNA was then isolated following the DNeasy Blood and Tissue protocol (Qiagen, Valencia, CA). A final DNA elution step was carried out with a 100-µL volume. The DNA was stored at −20° C. until the day of quantitative PCR (qPCR).

Extracted DNA was subjected to quantitative, real-time PCR. qPCR plates were prepared on the day of the assay. Standard amounts of conidia were prepared by hemacytometer counts, were spiked into blank uninfected lungs, and were used for generating standard curves. The results of qPCR are therefore reported as conidial equivalents (CE) per mL of primary lung homogenate. Samples were assayed in duplicate or triplicate using a Bio-Rad CFX96 real-time system (Hercules, CA). A single copy gene, Fks1, was chosen for quantitation. Primer sequences included the following: forward primer (5'-GCCTGGTAGTGAAGCT-GAGCGT-3' (SEQ ID NO: 3)), reverse primer (5'-CGGT-GAATGTAGGCATGTTGTCC-3' (SEQ ID NO: 4)), and probe (6-carboxyfluorescein [FAM]-AGCCAGCGGCCCGCAAATG-MGB-3' (SEQ ID NO: 5)) (Integrated DNA Technologies, Coralville, IA). The fks1 mutation (EMFR S678P) was not located in the primer-probe area of the genome and did not affect the quantitation reaction for that isolate. The primer-probe set was validated for all isolates by determining the kinetics and quantitative results for known quantities of conidia over the dynamic range ($10^2$ to $10^8$) (data not shown). Additionally, conidium-spiked uninfected lung homogenate was used to test for the presence of PCR inhibitors that may adversely affect qPCR results.

The cycling conditions were as follows: activation, 50° C. for 2 min; heat inactivation, 95° C. for 10 min for 1 cycle; denaturation, 95° C. for 15 s; annealing and extension, 65° C. for 1 min for 40 cycles. Quantitation standards were run in conjunction with each set of samples. The threshold cycle ($C_T$) of each sample was interpolated from a five-point standard curve of $C_T$ values prepared by spiking uninfected mouse lungs with known amounts of conidia ($10^3$ to $10^7$) from each isolate being tested. Results were reported as the number of conidial equivalents (CE) per milliliter of lung homogenate. Untreated control mice 7.4 log log 10 CE/ml of lung homogenate at the end of the study period.

Disseminated infection with *C. auris* B11211 infection was produced by injection of 0.1 ml of the inoculum via the lateral tail vein 2 h prior to the start of antifungal therapy. At the end of the study period (8 h), animals were sacrificed by $CO_2$ asphyxiation. After sacrifice the kidneys of each mouse were immediately removed and placed in sterile 0.15 M NaCl at 4° C. The organs were homogenized and then serially diluted 1:10. Aliquots were plated onto SDA for viable fungal colony counts after incubation for 24 h at 35° C. The lower limit of detection was 100 CFU/kidney. The results are expressed as the mean and standard deviation of the $\log_{10}$ CFU/kidney from three mice. Disseminated *C. albicans* K1 infection with produced in the similar manner.

Single Dose Drug Treatment. Groups of mice were treated with intraperitoneal single of turbinmicin at 16, 32, 48, and 64 mg/kg (*C. albicans* K-1) or 8, 16, 32, and 64 mg/kg (*C. auris* B11211). Control mice were treated with saline. Groups of mice were sacrificed at the start of therapy and 6 hours after therapy for determination of organism burden in the kidney as described above.

Multi-Dose Drug Treatment. Groups of mice infected by *C. auris* B11211 or *C. albicans* K1 were treated with turbinmicin at 1, 2, 4, and 8 mg/kg by an intraperitoneal route every 6 h or every 8 h in 24 h. Control mice were treated with saline. Groups of mice were sacrificed at the start of therapy and 24 hours after therapy for determination of organism burden in the kidney as described above.

Groups of mice infected by *A. fumigatus* F11628 were treated with turbinmicin at 0.25, 0.5, and 1 mg/kg by an intraperitoneal route every 6 h or every 8 h for the 4-day experiment. Groups of mice were sacrificed at the start of therapy and 4 days after therapy for determination of organism change of log 10 CE/mL of lung homogenate over the treatment period.

Figure 8A:
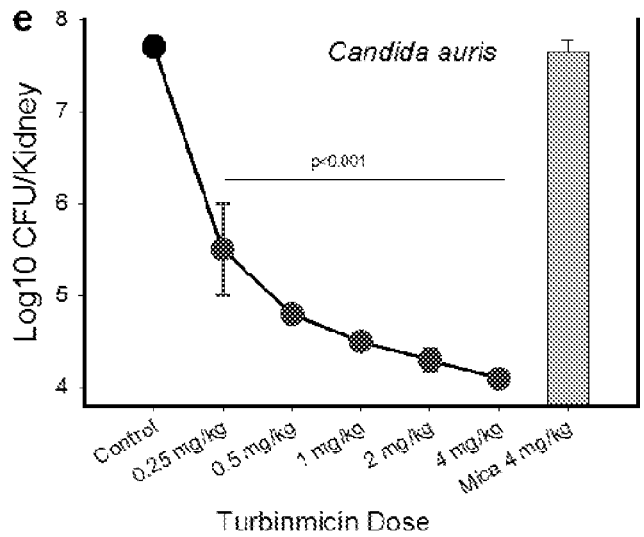
FIGS. 8A-B show graphs of in vivo multi-dose experiments with turbinmicin against (8A) *Candida auris* B11211 and (8B) *Aspergillus fumigatus* F11628 using an aspiration pneumonia model. Multi-dose experiments used administration of turbinmicin at doses of 0.25, 0.5, or 1 mg/kg at 6 h intervals (over a 4 day period) by IP.

Results. A multi-dose experiment with *C. auris* B11211 infection murine model was evaluated, and four doses (1, 2, 4, and 8 mg/kg) of turbinmicin were administered to mice every six hours over a 24 h period; turbinmicin was administered by intraperitoneal route. At 24 h, in vivo efficacy was observed at all concentrations in a dose-dependent manner (>3-log 10 CFU/kidney reduction) (FIG. 7C, FIG. 8A). Turbinmicin also showed in vivo efficacy against *C. albicans* K1 for a single dose experiment with administrations of 16, 32, 48 and 64 mg/kg turbinmicin (FIG. 7A) as well as the multi-dose treatment (1, 2, 4, and 8 mg/kg) over 24 hours (>1-log 10 CFU/kidney reduction) (FIG. 7B). Single dose experiments with *C. auris* (data not shown) infected mice failed to reveal a significant antifungal effect.

Figure 8B:
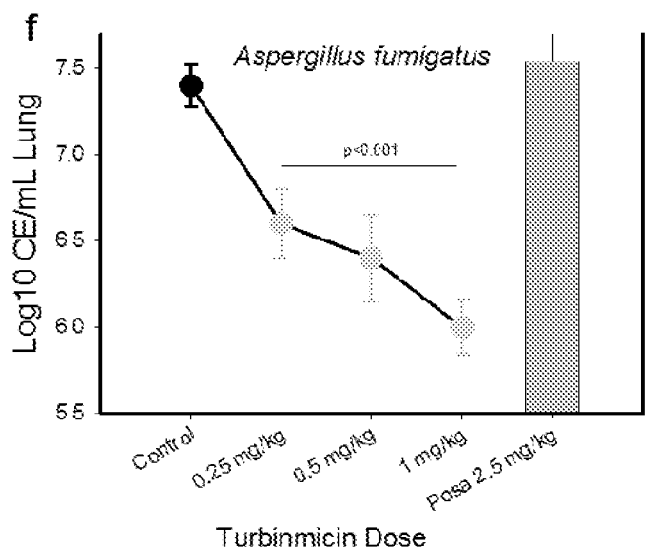

Given the in vitro potency of turbinmicin against the pan azoles-resistant strain *A. fumigatus* F11628 (Cyp51 mutant), we evaluated the in vivo efficacy of turbinmicin in an in vivo model of invasive pulmonary Aspergillosis. Following infection, mice were given 0.25 to 1 mg/kg of body weight by IP every 6 hrs for 4 days. Efficacy was assessed by quantitative PCR (qPCR) of lung homogenate and survival. At the start of therapy, mice had 4.64±0.21 $\log_{10}$ CE/mL of lung homogenate, and the infectious burden increased to 7.31±0.23 $\log_{10}$ CE/mL of lung homogenate in untreated animals at the end of the study (4 days). Dose-dependent activity was observed with the 100% survivals for all the three dosages, and 1-log 10 CE/mL reduction measured by qPCR was reached at the dose of 1 mg/kg (FIG. 8B). As comparison, posaconazole, the most recently approved advanced-generation triazole with potent anti *Aspergillus* activity, required much higher dose values (150 mg/kg/24 h) to achieve 1-log kill for the same Cyp51 mutant *A. fumigatus* strain. Consequently, turbinmicin has tremendous promise as an antifungal therapeutic by virtue of its potent antifungal activity.

Equivalents

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A compound having the structure of Formula I, Formula II, or a stereoisomer thereof, in isolated form

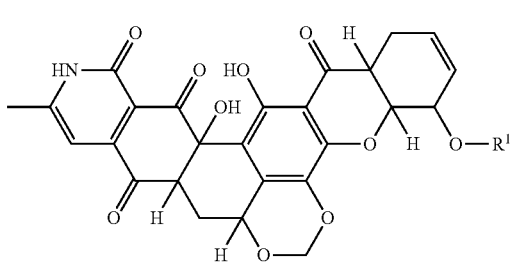

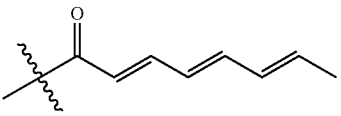

wherein:

$R^1$ is in Formula I;

$R^1$ is C(O)—$R^2$ in Formula II, wherein $R^2$ is a substituted or unsubstituted alkyl or alkenyl group;

provided that $R^1$ is not 1-oxo-oct-2,4,6-trienyl.

2. The compound of claim 1, having the structure of Formula IA:

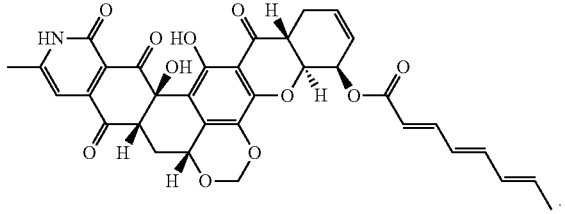

IA

3. The compound of claim 1, wherein the compound has the structure of Formula IIA:

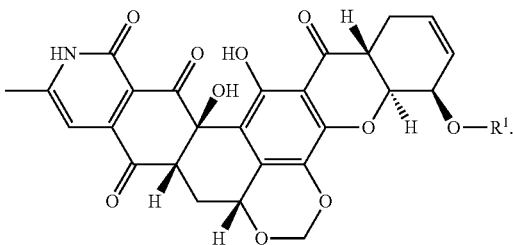

IIA

4. The compound of claim 1, wherein $R^2$ is an unsubstituted alkyl group.

5. The compound of claim 1, wherein $R^2$ is an unsubstituted $C_{5-9}$ alkyl group.

6. The compound of claim 1, having a purity of at least 90 wt %.

7. A pharmaceutical composition comprising a pharmaceutically acceptable carrier and an effective amount for treating a fungal infection of a compound of claim 1.

8. The pharmaceutical composition of claim 7, wherein the pharmaceutical composition is formulated for oral, parenteral, nasal, or topical administration.

9. The pharmaceutical composition of claim 7 further comprising a second antifungal agent or combination of antifungal agents different from turbinmicin.

10. The pharmaceutical composition of claim 9, wherein the second antifungal agent or combination of antifungal agents is selected from the group consisting of azoles, echinocandins, and polyenes.

11. The pharmaceutical composition of claim 9, wherein the second antifungal agent or combination of agents is selected from the group consisting of amphotericin B, flucytosine, fluconazole, voriconazole, posaconazole, isavuconazole, micafungin, cyphomycin, and forazoline.

12. The composition of claim 7, wherein the carrier comprises aqueous DMSO.

13. The composition of claim 12, wherein the carrier comprises a mixture of at least about 1 wt % DMSO in phosphate buffer solution.

14. The composition of claim 12, wherein the carrier comprises a mixture of about 1 wt % to about 80 wt % DMSO in phosphate buffer solution.

15. A method of treating a fungal infection comprising administering to a mammal in need thereof an effective amount of the compound of claim 1 or the pharmaceutical composition of claim 7.

16. The method of claim 15, wherein the mammal is human and/or the effective amount of the compound is 0.01 to 100 mg/kg of body weight of the mammal.

17. The method of claim 15, wherein the fungal infection is caused by one or more of *Candida, Fusarium, Scedosporium, Rhizopus, Mucor, Apophysomyces, Lichteimia, Cynninghamella* or *Aspergillus*.

18. The method of claim 15, wherein the fungal infection is caused by one or more of *Candida albicans, Candida glabrata, Candida auris, Candida tropicalis, Rhizopus delemar, Mucor circinelloides, Apophysomyces elegans, Lichteimia corymbiferea, Aspergillus fumigatus*, and drug-resistant strains thereof.

19. The method of claim 16 wherein the effective amount of the compound is 0.1 to 10 mg/kg of body weight in the mammal.

20. The method of claim 15, wherein a second antifungal other than the compound of Formula I is administered to the mammal in need thereof simultaneously, sequentially or separately with the compound of Formula I, or the pharmaceutical composition.

21. A method of inhibiting growth of a biofilm comprising one or more of *Candida* or *Aspergillus*, the method comprising contacting the biofilm with an effective amount of a compound of claim 1.

* * * * *

UNITED STATES PATENT AND TRADEMARK OFFICE
CERTIFICATE OF CORRECTION

PATENT NO. : 12,240,859 B2
APPLICATION NO. : 17/420117
DATED : March 4, 2025
INVENTOR(S) : Timothy Bugni et al.

Page 1 of 1

It is certified that error appears in the above-identified patent and that said Letters Patent is hereby corrected as shown below:

In the Claims

In Column 26, Claim 12, Line 10, please delete "The composition" and insert --the pharmaceutical composition--

In Column 26, Claim 13, Line 12, please delete "The composition" and insert --the pharmaceutical composition--

In Column 26, Claim 14, Line 15, please delete "The composition" and insert --the pharmaceutical composition--

Signed and Sealed this
Twenty-ninth Day of April, 2025

Coke Morgan Stewart
*Acting Director of the United States Patent and Trademark Office*

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

```
<400> SEQUENCE: 1
gagtttgatc ctggctcag                                              19

<210> SEQ ID NO 2
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 2
ggttaccttg ttacgactt                                              19

<210> SEQ ID NO 3
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
gcctggtagt gaagctgagc gt                                          22

<210> SEQ ID NO 4
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
cggtgaatgt aggcatgttg tcc                                         23

<210> SEQ ID NO 5
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 5
agccagcggc ccgcaaatg                                              19
```